(12) United States Patent
Ten Eyck et al.

(10) Patent No.: US 7,927,269 B2
(45) Date of Patent: Apr. 19, 2011

(54) PATIENT CARESTATION

(75) Inventors: Lawrence G. Ten Eyck, Ellicott City, MD (US); Steven M. Falk, Baltimore, MD (US); Lynn E. Lynam, Kingsville, MD (US); Matthew L. Severns, Gaithersburg, MD (US); Amy V. Lindsey, legal representative, Kensington, MD (US); Michael H. Mackin, Ellicott City, MD (US)

(73) Assignee: General Electric Company, Schenectady, NY (US)

( * ) Notice: Subject to any disclaimer, the term of this patent is extended or adjusted under 35 U.S.C. 154(b) by 1 day.

(21) Appl. No.: 12/387,538

(22) Filed: May 4, 2009

(65) Prior Publication Data

US 2009/0240098 A1 Sep. 24, 2009

Related U.S. Application Data

(63) Continuation of application No. 10/808,971, filed on Mar. 25, 2004, now abandoned.

(51) Int. Cl.
*A61G 10/00* (2006.01)
(52) U.S. Cl. .......................................................... 600/21
(58) Field of Classification Search .............. 600/21–22, 600/300–301, 523; 705/3; 340/573.1, 691.6
See application file for complete search history.

(56) References Cited

U.S. PATENT DOCUMENTS

2002/0196141 A1 * 12/2002 Boone et al. .................. 340/540

FOREIGN PATENT DOCUMENTS

WO    WO 02/45566    *    6/2002

* cited by examiner

*Primary Examiner* — John P Lacyk
(74) *Attorney, Agent, or Firm* — Roger M. Rathbun (57) ABSTRACT

A patient carestation for providing care to a patient including at least one environmental sensor sensing information concerning the environment surrounding the patient and providing electronic signals indicative of that environment. There are also physiological sensors sensing information relating to physiological conditions of the patient other than skin temperature and providing electronic signals indicative of physiological conditions of the patient. There may also be therapeutic sensors providing data based on therapy administered by peripheral apparatus and an input receiving patient information. A signal processor receives the signals from the physiological sensors, the environmental sensor, the therapeutic sensor and the patient information input and combines those signals into an integrated combination of signals for use by the caregiver. The integrated combination of signals can be used in a smart alarm or to generally appraise the caregiver at a central location as to the status of the patient.

19 Claims, 4 Drawing Sheets

PATIENT CARESTATION

The present patent application is a continuation application of U.S. Ser. No. 10/808,971, filed Mar. 25, 2004, now abandoned entitled "PATIENT CARESTATION" and priority to that patent application is hereby claimed and the entire disclosure and specification of the prior application is hereby incorporated herein in its entirety by reference.

BACKGROUND

The present invention relates to a patient carestation, such as an infant carestation and, more particularly, to an apparatus having an integrated signal processing unit that receives disparate signals representing physiological information of a patient, such as an infant, as well as environmental conditions surrounding the infant being attended to by that infant care apparatus and/or other information relevant to the care of the infant.

Presently there are various differing types of patient care apparatus, particularly infant care apparatus, including incubators, warmers or combinations thereof. For example, an infant incubator is shown and described in U.S. Pat. No. 4,936,824 of Mackin et al; an infant warmer is shown and described in U.S. Pat. No. 5,474,517 of Falk et al and a combination apparatus combining the functions of an incubator and an infant warmer is shown and described in U.S. Pat. No. 6,224,532 of Jones et al and U.S. Pat. No. 6,231,499 of Jones et al.

With the use of such apparatus, it is typical to have certain sensors that detect various physiological conditions of the infant and the signals representative of those physiological conditions are sent to one or more monitors that provide a read out of that particular physiological condition. Typically, some of the physiological conditions are actually integrated into the infant care apparatus itself, such as patient skin temperature, where the skin temperature sensor is affixed to the infant and the signal representative of the infant skin temperature is directly sent to the infant care apparatus itself and normally used in a control algorithm to control the amount of heat provided to the infant.

There are other sensors, however, that also sense a particular physiological condition of the infant and those signals may or may not be integrated into some control or other circuitry within the infant care apparatus. More typically, such physiological sensors provide signals representative of a particular physiological condition via wires to a separate monitor where that condition is displayed and alarm functions are used to allow a continual visual display of the condition and activate an alarm if that condition exceeds certain norms. Accordingly, in order to carry out the monitoring of an infant, there may be numerous individual monitors and displays that are needed to enable the caregiver to continually have an overview of the well-being of the infant.

Within the normal hospital nursery, therefore, there are a vast number of monitors that receive data streams from sensors that sense, record and/or display the particular physiological condition sensed, and such physiological monitors can include sensors and monitors to sense and display weight, ECG, EEG, respiration, arterial blood pressure, non-invasive blood pressure, blood oxygenation, end tidal $CO_2$ concentration, patient skin temperature, electronic images such as x-ray data, ultrasound, nmr and the like.

Each of those physiological sensors and monitors surround the infant care apparatus or are in close proximity thereto and which crowd the hospital nursery and make working conditions difficult with the myriad of wires, tubes and the like. It is difficult for the caregiver to take note of the different monitors located in separate locations in the nursery and the vast array of monitors creates a working environment that is cluttered with the inevitable wires and tubes to attach the various sensors to the monitors. The data from such physiological sensors generally is not seen by the infant care apparatus itself nor integrated with any other sensed signals even though one or more of such physiological monitors may be physically mounted to the infant apparatus.

In addition to sensors providing streams of data relating to some physiological condition of the infant, there are also normally present sensors that sense certain environmental conditions surrounding the infant, such as air temperature, $O_2$ concentration and humidity.

The environment sensors sense conditions of the environment surrounding the infant, that is, the conditions that are normally created, in the most, by equipment that is affecting those conditions. Thus, the data from the environmental sensors may provide information that is somewhat, but not necessarily, indicative of the performance of the infant apparatus that is providing the support to the infant.

As a further type or classification of information or data that is of use in treating a patient, there is therapeutic data and which generally relates to certain peripheral equipment that may be providing some therapeutic treatment to the patient and which may include the use of a ventilator that is breathing for the patient, including the administration of inhaled nitric oxide, or an IV pump that is administering fluids to the patient. Therefore, the therapeutic data includes information relating to that peripheral equipment and may include, for example, airway pressure, airway flow, tidal volume, partial pressure of gases inhaled and drip rate, identity and concentration of fluids being administered and the like.

An additional type or class of information or data that is used in the care of a patient is basically the patient information, such as medical history, pharmalogical information and the like and such information relates to the patient and may be inputted at the patient location by a caregiver or remotely provided by some central data base, such as the hospital central data system. Typically, the patient information can include the patient history, lab data from the analysis of patient fluids such as CBC, bilirubin, electrolytes, hematocrit, as well as information relating to allergies, prior treatment, drugs administered, current treatment, therapy administered, risk/history data, clinical findings and the like.

Not only is the number and type of monitors and inputs for physiological conditions, environmental conditions, therapeutic conditions and patient information of the infant varied, but the signals themselves may also be varied, that is, some of the electronic signals may be in digital form, others in analog form and some may be coded to the particular monitor so that all of the signals are not of a common type or stream of electronic data.

There has been, in the past, an infant care apparatus that received, from separate transducers, signals representative of the patient's skin temperature and the concentration of oxyhemoglobin in the infant's blood via oximetry, and provided those signals in a stream of data at an outlet of the infant care apparatus, for instance at an RS232 plug, however, even with that infant care apparatus, the environment surrounding the infant was not taken into consideration and which can be affected by the performance and functioning of the infant care apparatus itself or by some peripheral equipment. In addition, while the information and data may have been available, there was no attempt to make use of the combined information and data to enhance the quality of care being provided to the infant.

Other apparatus have individually sensed one physiological condition of an infant i.e. the skin temperature and one environmental parameter indicative of the performance of an infant care apparatus i.e., air temperature, however, there has been no attempt to combine the stream of electronic signals from a plurality of physiological sensors, other than patient skin temperature, with a stream of electronic signals from at least one environmental parameter sensor, or other information inputs into a unified, integrated stream of information in electronic form and to make use of the diverse information that is thereby available in that combination of electronic signals despite a clear need and use for the combined stream of data and information.

Thus, in effect, there are streams of data relating to the environment of the infant, the physiological condition of the infant, therapeutic data and patient data however those streams of data are maintained separate and go off in a variety of directions from the infant care apparatus to separate monitors or to some storage location and, therefore, provide only a partial, somewhat disjointed picture of the function and operation of the apparatus as well as the wellbeing of the infant since the caregiver cannot see the overall picture by having all of the relevant data and information available at one convenient location.

As such there are, therefore, a myriad of monitors and sensors that continuously ascertain the various types or classes of data and information relating to the patient, distributed in various locations about the nursery or other hospital location, however, there has been no attempt to combine the disparate signals into an integrated stream of data and to use the integrated stream of data in a form that is compatible in order to evaluate the infant or the apparatus, or both. Without that central integration circuitry that can process the various signals that carry data and information from the differing sensors and inputs to a integrated signal processor, there is, obviously, no way that a user can gain the important insight that can be derived from utilizing all of the various types of data and information to evaluate the apparatus and/or the infant.

For example, the combined data and information from an infant incubator environmental conditions and physiological information for an infant can be used as a confirmation of various multiple signals to allow faster clinical actions and less clinical errors to be determined by providing integrated steps or data representative of both the physiological information as to the patient and the environmental information relating to certain parameters of the apparatus. That information can, in integrated form, be used to glean considerably more information than with the present situation where the individual signals from each different sensor are individually used in multiple monitors that may not even be proximate to each other.

As an example, information from a physiological sensor, such as an ECG sensor can provide data as to the heart rate of the patient, evidence typically associated with determining bradycardia, and the information from a therapeutic sensor relating to the airway pressure of a ventilator can also be obtained and which may show a lower inspiratory pressure than the set pressure, thus by having the combination of information available by an integrated stream of data and information, the data can be assimilated by a signal processor in, for example, an infant care center, to interpret that data and flash a message to the clinician to check the ventilator for a malfunction, leak or a partial detachment from the patient airway. Individually, at the present, those different sensed values are located at separate, spaced apart monitors may not allow the clinician to respond as rapidly.

As a further example, the patient skin temperature, normally a item of information or data available at the infant care apparatus, can provide an indication that the patient skin temperature is descending and which is another symptom of bradycardia and it would also be advantageous to have that data and information available in an integrated stream of information and data for use by the clinician or other circuitry to interpret the data so as to be available to the clinician in a visually perceptible means for the clinician or by a signal processor or the like to interpret and use the various data and information.

Thus, it would be advantageous to have some means of integrating data relating to a plurality of differing modalities, that is, at least two physiological conditions of the infant, where those physiological conditions are some conditions other than infant skin temperature, the data relating to the environment surrounding the infant, the data indicative of the therapy provided by peripheral equipment and information relating to the patient at one location and to provide signal processing at that location on or built into an infant carestation to be able to process all of the available data in the signals from the variety of sensors and inputs and integrate all of that incoming data into a united, centrally located stream of data that can be used in various ways, including in a monitor that provides a visual perceptible indication of that integrated information that is of use to the caregiver.

It would therefore be advantageous in such infant carestation that there be some means to integrate all of the disparate signals from a myriad of individual sensors, including a plurality of sensors that sense physiological information of the patient, other than patient skin temperature, as well as at least one environmental condition such as a performance parameter of the infant care apparatus or other information in order to have a integrated, usable stream of information and data representative of the environmental and physiological conditions of the infant as well as patient data and therapeutic data.

It would be further advantageous in an infant carestation to have some diagnostic apparatus that can actually interpret the aforementioned diverse data and information to provide better care for the infant, whether in a more accurate diagnosis of a problem with the infant or the equipment assisting the infant or in providing a faster analysis of the conditions of the infant or the equipment in order to better care for the wellbeing of that infant or equipment.

SUMMARY OF THE INVENTION

Accordingly, the present invention relates to a patient carestation, particularly an infant carestation that provides the caregiver with local access to a diverse collection of data and information to aid in the treatment and care of a patient in a clinical setting.

By definition, the carestation, be it adult or infant, may have the following features: (1) common user interface presentation for monitors, devices, information and parameters including both inputs and outputs; (2) mechanical controls and displays ergonomically placed where the caregiver needs them; (3) a platform that provides for future expansion and upgrades; (4) connectivity capability to a central station monitor, that is, single or multiple device connections to the network, representing our or more patients; (5) monitoring of patient parameters and/or monitoring of therapeutic interventions, e.g. (a) physiologic parameters (b) hemodynamic, neurological, chemistry's, cardiologic (c) blood gases, lung mechanics, airway pressure and flow etc. (d) anesthetic gases (e) drug interventions and the like and (5) integrated communication.

The infant carestation has, incorporated therein, a signal processing circuitry or signal processing means that can receive as inputs, outputs from individual sensors where the sensors include at least two physiological sensors other than infant skin temperature, at least one environmental condition sensor as well as, possibly, of therapeutic data and information and other patient information and convert and integrate the data and information from the differing sensors and inputs into an integrated stream of electronic signals containing information and data relative to the wellbeing of the infant. The infant care center can also receive and integrate additional data and information from other sources, such as data and information relating to therapeutic treatment provided by peripheral apparatus and patient information.

As such, with the present invention, there is an infant carestation that provides a basis or central location where signals from the various sensors and inputs, both from the at least one environmental sensor and the at least two physiological sensors, as well as therapeutic and patient information, can be received and integrated into a single stream of usable electronic data that is available to the caregiver to analyze that data and to use that data for caring for the infant.

Once the integrated stream of electronic signals containing the data and information from at least two physiological conditions of the infant, other than skin temperature, at least one environment condition surrounding the infant as well as therapeutic and patient information has been achieved, the integrated stream of data and information can be routed to a visual display where that various data and information can be visually perceived by the caregiver. Thus one brain or controller on or affixed to the infant care center is looking at all of the vast variety of data and information relating both to multiple physiological conditions of the infant, as environmental conditions surrounding the infant as well as possible patient information and therapeutic information. Alternatively, or additionally, the integrated stream of information and data can be sent to a central storage facility in a hospital where the complete records of the infant are maintained and the integrated stream of data and information can be charted along with other information relative to the infant.

As a further feature, the integrated stream of information and data can be transmitted to a smart alarm that uses that information and data to provide a diagnosis as a tool to the caregiver to inform that caregiver of the likely cause for certain abnormal conditions. Basically the smart alarm is capable of carrying out (1) the integration of data and capability to prioritize multiple alarms to yield the critical ones, (2) the integration of data and capability to highlight the user to the alarms that need first response, (3) the integration of data and capability to prevent false alarms, (4) the integration of data and capability to more clearly define the alarm condition of the patient and (5) the integration of data and capability to prompt, or suggest, action to the caregiver depending upon alarms, data and history.

Thus with the present invention, as an additional benefit, the vast number of diverse monitors is eliminated and the caregiver does not have to look in multiple directions in order to obtain the information relating to the status of the infant and, to some extent, the functioning of the infant care apparatus as well as that of other peripheral apparatus being employed in maintaining the wellbeing of the infant. The normal clutter of the nursery is therefore greatly reduced by combining and providing the integrated diverse electrical signals relating to the physiological and environment conditions, as well as therapeutic and patient information, that are being monitored by the infant care center that can be readily seen at a single location and there is less stress on the caregiver who does not have to constantly scan in all directions to be assured that the infant is being properly monitored.

These and other features and advantages of the present invention will become more readily apparent during the following detailed description taken in conjunction with the drawings herein.

DETAILED DESCRIPTION OF THE INVENTION

Figure 1:
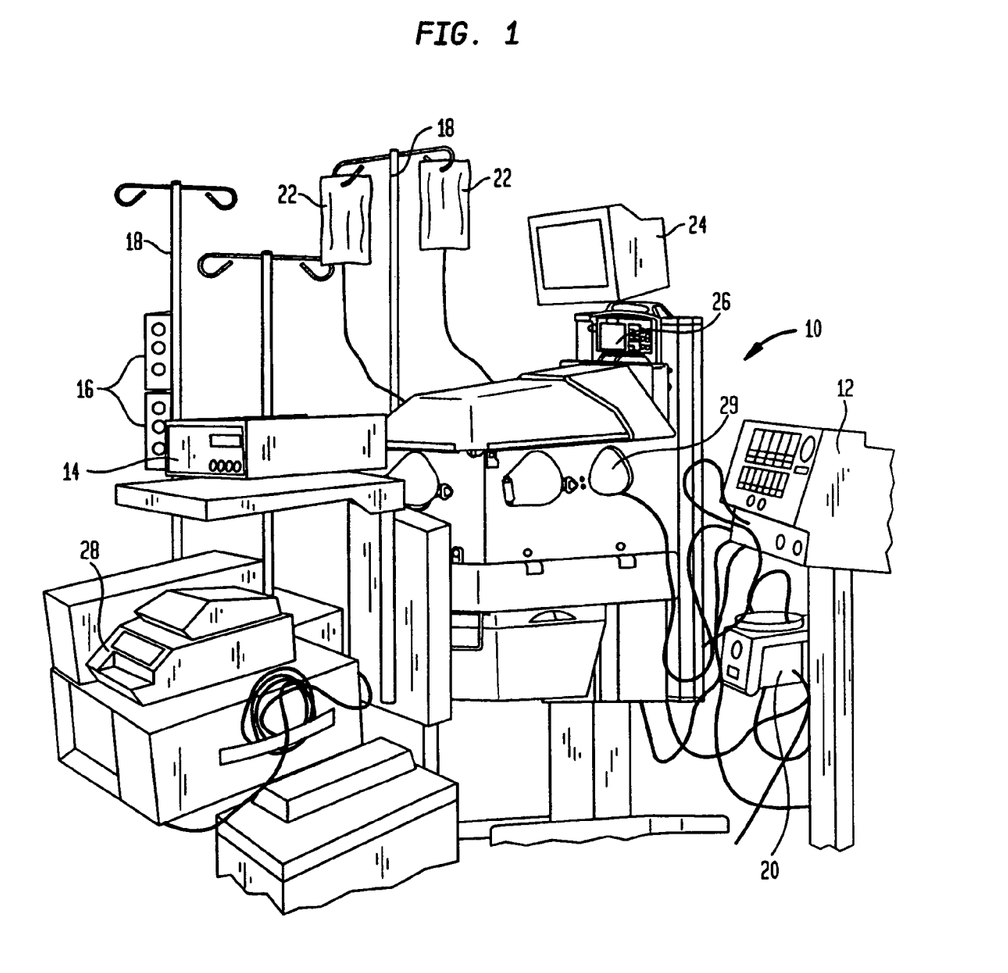
FIG. 1 is a schematic view of a typical hospital nursery room showing the attendant equipment that may be present.

Referring now to FIG. 1 there is shown a perspective view of a typical hospital nursery having an infant care apparatus 10 situated therein. As can be seen, the infant care apparatus 10 is normally surrounded by a number of individual monitors that sense various parameters relating to the environment surrounding or affecting the infant by the infant care apparatus 10 as well as other peripheral devices and apparatus that may also be carrying out certain functions on the infant, including an infant ventilator 12. In addition there are a number of sensors and monitors that are continually sensing the physiological conditions of the infant.

For example, as to physiological conditions of the infant, there may be an oximeter 14 that is sensing the oxygenated blood concentration of the infant. Also as can be seen, there can normally be one or more syringe pumps 16 that deliver a bolus of a medication to the infant and which can be mounted to an IV pole 18. Other equipment includes a humidifier 20 that provides humidification to the air delivered to the infant by means of the infant ventilator 12. With the infant ventilator 12, there may be one or more therapeutic sensors that gather data, for example, relating to the partial pressure of oxygen ($TcpO_2$) in the airway delivering air to the infant.

There can also be IV drip bags 22 suspended from an IV pole 18 and a visual display monitor 24 located atop of the upper area of the infant care apparatus 10 and, of course, the normal control and display module 26 that is incorporated into the infant care apparatus 10. Generally some patent skin temperature sensor (not shown) provides a signal stream representative of patent skin temperature to the control and display module 26 and is part of the normal functioning of the infant care apparatus 10.

There also can be seen an extracorporeal membrane oxygen unit 28 and in a normal nursery, that are likely to be found various other monitors and peripheral devices that are used in providing for the wellbeing of the infant, including, but not limited to ECG amplifiers, temperature probes, non-invasive blood pressure monitors, EEG monitors and the like, all used in the care of an infant and many of which require various preamplifiers and visual displays that are used with each individual monitor or sensor. Other sensors or sensing apparatus can include an x-ray machine having a plurality of detectors that can provide real time x-rays of the infant and provide those x-rays in the form of an electronic stream of signals. The can also be a scale that provides input as to the weight of the infant.

According, as can be seen, the overall nursery room is considerably cluttered with the multitude of sensors, monitors, preamplifiers, IV solutions, medication dispensers and the like not to mention the vast myriad of wires and tubes that are used in order to make the aforedescribed equipment functional. For example, a normal ECG monitor may have between 4 and 12 leads to the infant, an EEG monitor can have 6-10 leads, a pulse oximeter one lead that is relatively large and there are also tubes that carry the ventilation air to the infant as well as many tubes that may be supplying fluids to the infant. As such, there can by something in the range of 2 to 3 dozen lines that are coming out of the infant care apparatus 10 through the portholes such as the porthole 29 or, alternatively through a grommet provided in the infant care apparatus 10.

Some of the aforedescribed monitors and sensors are used to sense and determine various environmental conditions surrounding the patient and which are somewhat indicative of the performance of a piece of apparatus, that is, the performance of the infant apparatus in use for caring for the infant. Therefore, there may be a sensor that determines the air temperature surrounding the infant, as well as the oxygen concentration and humidity conditions in the infant's immediate environment and therefore provide environmental information to a monitor and/or visual display.

Additionally, for example, if a ventilator is being used, there can be a gathering of therapeutic data and information including one or more sensors on the airway to the infant that monitors the respiratory airway pressure, the airway flow in the airway and the like and the individual data is sent to some monitor where a visual display can be continuously be viewed by the caregiver.

Thus, the environmental monitors display the conditions under which the infant is being treated at the location of the infant and also serve as an indication, albeit sometimes indirect, of the functioning of the apparatus that is administering some means of care to the infant. Other of the sensors and monitors, as previously explained, monitor physiological conditions of the infant and still others monitor the therapeutic data such as may be indicative of the operation of peripheral equipment such as a ventilator or an IV pump. As further information, there is, of course patient information that is provided by the patient, the caregiver, or is embodied in the results of lab tests of the patient.

In any event, as can be seen, there ultimately exists a vast myriad of monitors, wires, tubes and the like and those monitors are located at differing positions around the infant care apparatus 10 such that it is difficult for the caregiver to monitor all of the different indications and data and each monitor is independent, that is, there is no attempt to use the data from one monitor to combine that data with data from another monitor to produce an integrated stream of data and information relating to differing sensors and inputs of information and then to take the next step of using the integrated stream of data and information to feed a smart alarm that can diagnose a problem in the care of the infant by using the differing data and information from the integrated stream of data and information.

Figure 2:
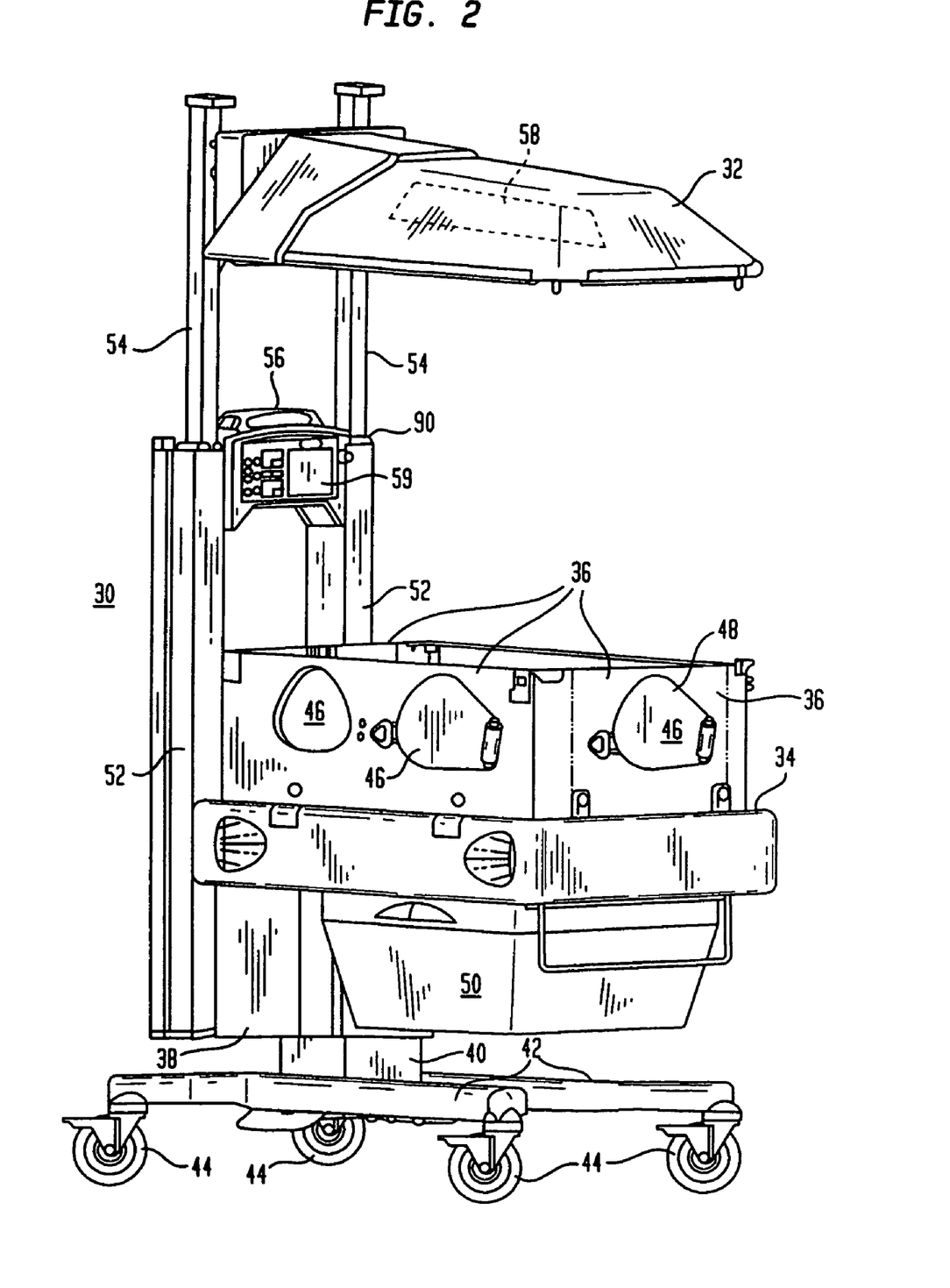
FIG. 2 is a perspective view of a typical infant care apparatus that can incorporate the present invention showing its canopy in the upper position.
Figure 3:
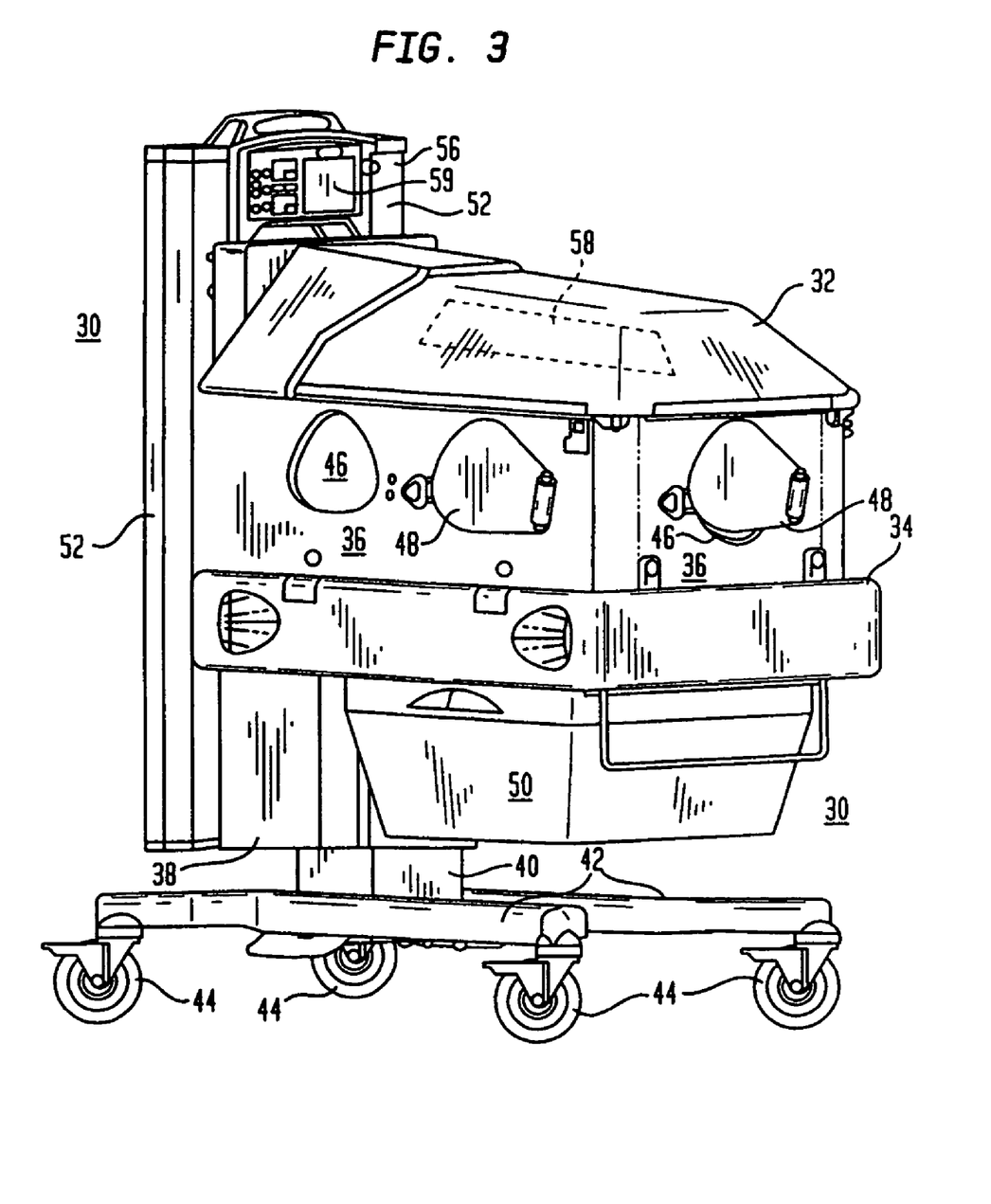
FIG. 3 is a perspective view of a typical infant care apparatus of FIG. 2 with its canopy in the lower position.

Turning now to FIGS. 2 and 3, there is shown an infant care apparatus 30 that can be used with the present invention to provide an orderly atmosphere in the hospital nursery while, at the same time, enhancing the flow of information and data to the caregiver that can combine the disparate monitors and sensors into an integrated stream of data and information concerning at least one environment condition of the infants surroundings and at least two physiological conditions of the patient, other than patient skin temperature and also therapeutic and patient information and data.

Basically, the FIGS. 2 and 3 apparatus is but one infant apparatus that can be used with the present invention since the present invention is applicable to any infant care apparatus that carries out thermoregulation of an infant and where there are numerous monitors present. The FIGS. 2 and 3 apparatus is, therefore, one illustration of such an infant care apparatus and which is shown and described in U.S. Pat. No. 6,224,539 of Jones et al and the disclosure of that patent is hereby incorporated herein by reference in its entirety.

Accordingly, in FIGS. 2 and 3, there is shown perspective views of an infant warming apparatus 30 constructed in accordance with the present invention with the canopy 32 in its upper position in FIG. 2 and in its lower position in FIG. 3. As will be understood, in the FIG. 2 position, the infant warming apparatus 30 acts as an infant warmer with considerable access to the infant for performing interventions on the infant and in the FIG. 3 configuration, the infant warming apparatus 30 acts as an incubator with the infant confined within an infant compartment providing a protective environment and having a controlled atmosphere to provide warmth as well as controlled humidity.

As shown, the infant warming apparatus 30 includes an infant platform 34 that underlies and supports an infant. As is also seen, a plurality of walls 36 are provided to contain the infant safely within the infant warming apparatus 30 and are located at all of the four sides of the infant platform 34. The walls 36 are preferable constructed of transparent plastic material and, as will be explained, cooperate with other components in order to provide an incubator function to the infant warming apparatus 30 when in the FIG. 3 configuration.

The infant platform 34 is mounted to a vertical movable base member 38 which, in the preferred embodiment, is movably affixed to a stationary vertical base member 40, which, in turn, is mounted to a base 42 having wheels 44 for ready movement of the infant warming apparatus 30.

The vertical movable base member 38 is preferably mounted so that the user can adjust the height of the infant platform 34 by raising and lowering the vertical movable base member 38 as desired, thus the infant platform 34 can be adjusted to the preferred height by the user. As further standard features, the walls 36 have handholes 46 to afford access to the infant when in the incubator configuration of FIG. 3, and which generally have doors 48 that can be opened to obtain access to the infant and, of course, closed when the particular intervention has been completed to preserve the desired environment surrounding the infant.

Another convenient feature includes a drawer 50 to retain supplies or other devices needed to carry out some operation on the infant and which is normally located beneath the infant platform 34. Other features include the maneuverability of the walls 36 that are pivotally mounted at their bases to the infant platform 34 such that the doors can be swung outwardly and downwardly and, as a further alternative, can be easily fully removed from the infant platform 34. As such, therefore, when the canopy 32 of the infant warming apparatus 30 is in its upper position as shown in FIG. 2, the walls 36 can be dropped downwardly or removed altogether so that the attending personnel can have unlimited access to an infant resting on the infant platform 34 to perform interventions on that infant.

Further structural components of the infant warming apparatus 30 include stationary frame members 52 that are affixed to the vertical movable base member 38 and, as shown, there are two vertical stationary frame members 52 in the preferred embodiment although there may be only one or there may be further numbers of such members. Two vertical movable frame members 54 are movably fitted into the stationary frame members 52 and which can be moved upwardly and downwardly by the user as will be explained.

A control module 56 is conveniently positioned intermediate the stationary frame members 52 and may include displays of various monitored parameters as well as include the various controls for operation of the functions of the infant warming apparatus 30.

As may now be seen in general, in the operation of the infant warming apparatus 30, the canopy 32, in the preferred embodiment, houses a radiant heater 58. The canopy 32 can be moved between its lower position as shown in FIG. 3 and its upper position as shown in FIG. 2 depending upon the mode of operation desired by the user. In the upper position of FIG. 2, the infant care apparatus 30 functions as an infant warmer where there is full access to the infant and where the overhead radiant heater 58 supplies heat to maintain the infant with sufficient warmth.

In the lower position of FIG. 2, the infant warming apparatus 30 functions as a normal incubator, since the outer periphery of the infant canopy 32 fits fully over the upper edges of the walls 36 to form therein, an infant compartment that is provided with warm air and controlled humidity in the normal functioning of an incubator.

There is a monitor 59 that is shown as built into the control module 56, however, it may also be provided on a shelf that is affixed to the infant warming apparatus 30. The monitor 59 is of the type that can display a multitude of differing inputs representing different information and data on different screens that can be selected by an appropriate menu so that the user can select any one or more of a particular input data to be displayed on the monitor 59.

In essence, the monitor 59 can accept an integrated stream of data and information from a vast myriad of disparate sensors that sense various parameters relating to the environment surrounding the infant as well as from sensors that sense a physiological condition of the infant and can display one or more of those inputs from such sensors by a selection process of the caregiver. Other inputs of information can include therapeutic inputted data and patient information.

That integrated stream of data and information that carries the electronic signals representative of both the environment parameters and the physiological condition of the infant are provided by a signal processor, not shown in FIGS. 2 and 3, and which is embodied in the infant warming apparatus 30.

Figure 4:
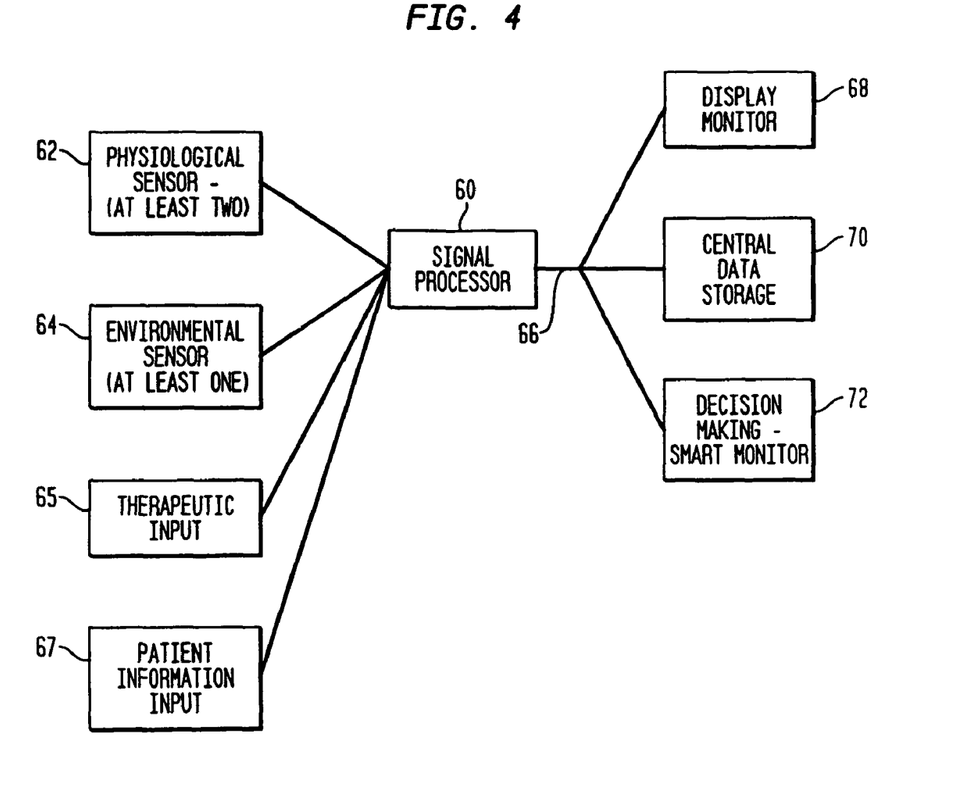
FIG. 4 is a block diagram of an embodiment of the present invention.

Turning now to FIG. 4, there is shown a block diagram of the various functions of the present invention to illustrate the scope of the present invention. In FIG. 4, therefore, there is a signal processor 60 that receives the signals from at least two physiological sensors 62, other than patient skin temperature, and those signals are representative of physiological conditions of the infant, including weight, EEG, ECG, respiration, arterial blood pressure, non-invasive blood pressure, blood oxygenation, end tidal Co2, patient skin temperature, and x-ray data and the like and the electronic signals representative of those individual sensors and sensed parameters of the physiological condition of the infant are transmitted to the signal processor 60. By reference to the at least two physiological sensors, other than skin temperature, it is meant that the third sensor may be a patient skin temperature sensor, however, however, there are at least two physiological sensors that sense a physiological condition of the patient other than skin temperature.

The same is true of the environmental sensors 64, and which include the air temperature in the vicinity of the infant, the humidity and the oxygen concentration of the environment surrounding the infant.

As also can be seen, there is a therapeutic input 65 that basically conveys the information and data to the signal processor 60 relating to the therapy administered to the infant by means of some peripheral equipment, such as from a ventilator or IV pump and which information may, therefore, include conditions within the airway to the patient for air delivered by the ventilator, such as airway pressure, airway flow, tidal volume, drugs administrated, drip rate and the electronic signals representative of those conditions are transmitted to the signal processor 60.

Additionally, there is a patient information input 67 that inputs information concerning the patient and which may be inputted directly from a sensor, by a caregiver, or may even be communicated from the central hospital data base which would include admission information concerning the patient, family history and the like. Other inputs relating to the patient and inputted by the patient information input could include data from the results of lab procedures carrying out analyses of a patient fluid such as CBC, bilirubin, electrolytes, hematocrit and the like.

The signal processor 60 thereby combines the disparate signals into a integrated stream of data and information that contains information and data relating to the at least two physiological conditions of the infant, other than skin temperature, as well as the environmental conditions surrounding the infant and also information relating to therapy provided by peripheral equipment and patient information. The signal processor 60 thus processes that electronic stream of information and data into an integrated output stream 66. In the event one or more of the input signals from the physiological sensors 62, the environmental sensor 64, the therapeutic input 5 or the patient information input 67 is in analog form, the signal processor 60 can include an analog to digital converter so that all of the stream of signals containing that information and data in the output stream can be in the same form i.e. digital.

Accordingly, the signal processor 60 that is located in the infant warmer apparatus 30 integrates all of the disparate signals from the various sensors used with the infant into an integrated stream of information and data and which contains information and data with respect to at least two physiological sensors 62 representative of physiological conditions of the infant, other than skin temperature, as well as signals from the environmental sensor 64 and which are representative of at least one environment condition under which the infant resides and which is also, generally, an indication of the performance of one or more devices providing care to the infant. The other data is provided by the therapeutic input 65 and the patient information input 67.

By means of the signal processor 60, the infant care apparatus 30 becomes the center of the monitoring communications, i.e. an infant care center and thus eliminates the myriad of individual monitors that otherwise would be spaced all around the infant care apparatus 30.

Therefore, there can be a display 68 that can be a part of the monitor 59 and which can display the various information and data from the different types of sensors, that is, the physiological sensors 62, the environmental sensors 64 as well as the therapeutic input 65 and the patient information input 67. Thus, the integrated stream of information and data, in electronic form, can be transmitted to the display 68 where the caregiver can visually become cognizant of all of the relevant information relating both to the infant's environment and the infant's physiological condition.

In addition, or alternatively, the integrated stream of information and data from the integrated output stream 66 can be transmitted to a central data storage 70 where the information and data can be preserved in a central repository within a hospital and included in the infant's record files.

As a still further alternative, the integrated stream of information and data from the integrated output stream 66 can be transmitted to a smart alarm 72 that can receive all of the disparate information and data and actually make decisions or recommended courses of action based on that variety of information to notify the caregiver of the possible causes of problems or diagnose the care being provided to the infant. For instance, the smart alarm 72 can analyze the disparate information and data and provide an analysis of a problem and suggest a solution based upon that information and data. Without the integrated stream of information and data available in the integrated output stream 66, the information necessary for analyzing the source of problem would not be possible and would simply not be available in a form that could be analyzed by a single monitor that can use the disparate information in a effective manner.

Those skilled in the art will readily recognize numerous adaptations and modifications which can be made to the integrated monitoring function of the infant care apparatus of the present invention which will result in an improved system, yet all of which will fall within the scope and spirit of the present invention as defined in the following claims. Accordingly, the invention is to be limited only by the following claims and their equivalents.

We claim:

1. A patient carestation adapted to be used in connection with a patient, said patient carestation providing a controlled environment surrounding a patient and having a monitor, at least one environmental sensor adapted to sense information concerning the environment surrounding a patient and to provide electronic signals to the monitor indicative of that environment, at least one physiological sensor adapted to obtain information relating to a physiological condition of a patient undergoing treatment on a patient support and to provide electronic signals to the monitor indicative of a physiological condition of the patient, said patient monitor having signal processing system to receive signals from the at least one environmental sensor and the at least one physiological sensor to integrate those signals into an integrated output stream of signals that convey information relating both to the environment surrounding the patient and a physiological condition of the patient, a smart alarm receiving the stream of integrated signals and adapted to generate multiple alarms, the smart alarm prioritizing the multiple alarms to yield a critical alarm wherein the integrated output stream of signals is converted into a prioritized readout visually recognizable by a user that provides a recommended course of action to a user based upon the information relating both to the environment surrounding the patient and a physiological condition of the patient.

2. The patient carestation as defined in claim 1 wherein a patient receives air through an airway and there is a therapeutic sensor that senses therapeutic information relating to conditions in the airway.

3. The patient carestation as defined in claim 1 wherein the therapeutic sensor senses information relating to the ventilation of a patient, including at least one of airway pressure, airway flow, tidal volume, and the concentration or partial pressure of gases in the airway.

4. The patient carestation as defined in claim 1 wherein said integrated output stream of signals is transmitted to a remote location by wireless telemetry.

5. The patient carestation as defined in claim 1 wherein said patient carestation is in an infant care apparatus.

6. The patient carestation as defined in claim 1 wherein the apparatus further includes an imaging device to provide electronic signals representative of an image of a patient and such signals are inputted to the signal processing system.

7. A method of providing an integrated stream of data and information in a patient carestation relating to an operational parameter of the patient care apparatus and a physiological condition of a patient, said method comprising the steps of:
   locating a patient carestation having a monitor in proximity to a patient to provide a controlled environment surrounding a patient:
   providing at least one environmental sensor adapted to provide an output signal indicative of at least one environmental parameter of the controlled environment surrounding the patient;
   providing at least one physiological sensor adapted to sense at least one physiological condition of a patient, and to provide an output signal to the monitor indicative of a physiological condition;
   integrating the output signals within the monitor from the at least one environmental sensor and the at least one physiological sensor to obtain and provide a combined integrated stream of data and information at the monitor indicative of both an environmental condition and a physiological condition of a patient,
   generating multiple alarms based on the integrated output signals, and
   prioritizing the multiple alarms based on criticality to yield a critical alarm and using the combined integrated stream of data and information to provide a prioritized readout visually recognizable by a user that provides a recommended course of action to a user based upon both a physiological condition sensed by the at least one physiological sensor and an environmental parameter sensed by the at least one environmental sensor.

8. The method as defined in claim 7 wherein the method further comprises the step of transmitting the combined integrated stream of data and information to a monitor to display the combined integrated stream of data and information in a visually perceptible form.

9. The method as defined in claim 7 wherein the step of providing at least one physiological sensor adapted to sense at least one physiological condition of a patient, comprises providing a physiological sensor adapted to sense at least one physiological condition from the group comprised of weight, ECG, EEG, respiration, arterial blood pressure, non-invasive blood pressure and blood oxygenation, end tidal $CO_2$, patient skin temperature and x-ray data.

10. The method as defined in claim 7 wherein the step of providing an environmental sensor comprises providing at least one environmental sensor adapted to sense a parameter from the group comprised of air temperature, oxygen concentration and humidity.

11. The method as defined in claim 7 wherein the method further comprises the step of providing to the monitor a therapeutic input including information relating to a peripheral apparatus including a ventilator or an IV pump.

12. The method as defined in claim 7 wherein the method further comprises the step of providing patient information to a patient information input of the monitor.

13. The method as defined in claim 7 wherein the method is used in an infant care apparatus.

14. A patient carestation for monitoring conditions of a patient under the care of a patient care apparatus providing a controlled environment surrounding a patient, said carestation comprising:
- a monitor,
- at least one environmental sensor adapted to sense an environmental condition of a patient cared for by the patient care apparatus and to send electronic signals to the monitor indicative of an environmental condition;
- at least one physiological sensor adapted to sense a physiological condition of a patient cared for by the patient care apparatus and to send electronic signals to the monitor indicative of a physiological condition of a patient;
- at least one therapeutic sensor adapted to sense a therapy condition relating to the administration of care to a patient by a peripheral apparatus;
- the monitor having an input for receiving patient information relating to a patient in the form of electronic signals;
- the monitor having a signal processor adapted to receive electronic signals from the at least one environmental sensor, the at least one physiological sensor, the at least one therapeutic sensor and the electronic signals representative of patient information received by said input, said signal processor integrating said electronic signals into an integrated stream of electronic signals; and
- a smart alarm adapted to receive the integrated stream of electronic signals to generate multiple alarms, the smart alarm prioritizing the multiple alarms based on the criticality of the electronic signals from the at least one environmental sensor, the at least one physiological sensor, the at least one therapeutic sensor and the electronic signal representative of patient information to yield and visually display a prioritized alarm.

15. The patient carestation as defined in claim 14 wherein a patient receives air through an airway and the at least one therapeutic sensor senses therapeutic information relating to conditions in the airway.

16. The patient carestation as defined in claim 15 wherein a patient receives air through said airway by means of a ventilator.

17. The patient carestation as defined in claim 15 wherein the at least one therapeutic sensor senses information relating to the ventilation of a patient from the group comprising airway pressure, airway flow, tidal volume, and the concentration or partial pressure of gases in the airway.

18. The patient carestation as defined in claim 14 wherein the at least one environmental sensor senses at least one environmental condition from the group comprised of air temperature, oxygen concentration and humidity.

19. The patient carestation as defined in claim 14 wherein the at least one physiological sensor comprises at least one physiological sensor that senses at least one condition from the group comprising weight, ECG, EEG, respiration, arterial blood pressure, non-invasive blood pressure, blood oxygenation, end tidal $CO_2$ concentration, patient skin temperature and electronic images.

* * * * *